(12) United States Patent
Fukushima et al.

(10) Patent No.: US 8,080,605 B2
(45) Date of Patent: Dec. 20, 2011

(54) POLYMER-FILLER COUPLING ADDITIVES

(75) Inventors: Yasuo Fukushima, Kodaira (JP);
William L. Hergenrother, Akron, OH
(US); Russell W. Koch, Hartville, OH
(US)

(73) Assignee: Bridgestone Corporation, Tokyo (JP)

( * ) Notice: Subject to any disclaimer, the term of this patent is extended or adjusted under 35 U.S.C. 154(b) by 794 days.

(21) Appl. No.: 11/617,210

(22) Filed: Dec. 28, 2006

(65) Prior Publication Data
US 2007/0161756 A1  Jul. 12, 2007

Related U.S. Application Data

(60) Provisional application No. 60/754,533, filed on Dec. 28, 2005.

(51) Int. Cl.
*C08K 3/18* (2006.01)
*C08C 19/20* (2006.01)

(52) U.S. Cl. ........ 524/430; 524/445; 524/449; 524/451; 525/194; 525/195; 525/232; 525/349; 525/375; 525/383; 568/21; 568/22; 568/23; 568/25; 544/53; 544/63; 544/72; 544/88

(58) Field of Classification Search .......... 524/89, 524/86, 449; 525/349, 375, 383, 194, 195, 525/232; 568/21, 22, 23, 25; 544/53, 63, 544/72, 88
See application file for complete search history.

(56) References Cited

U.S. PATENT DOCUMENTS

| | | | | |
|---|---|---|---|---|
| 4,130,562 | A * | 12/1978 | Dubs et al. | 548/186 |
| 5,109,055 | A | 4/1992 | Nagasaki et al. | |
| 5,230,982 | A * | 7/1993 | Davis et al. | 430/138 |
| 5,248,722 | A | 9/1993 | DeTrano et al. | |
| 5,514,756 | A * | 5/1996 | Hsu et al. | 525/332.5 |
| 5,726,237 | A | 3/1998 | Satoh et al. | |
| 6,552,060 | B1 * | 4/2003 | Kirkpatrick | 514/398 |
| 6,596,798 | B1 | 7/2003 | Rademacher et al. | |
| 6,649,684 | B1 | 11/2003 | Okel | |
| 6,740,151 | B2 * | 5/2004 | Belmont et al. | 106/31.6 |
| 7,186,845 | B2 | 3/2007 | Fukushima et al. | |
| 2008/0300368 | A1 * | 12/2008 | Miyazaki | 525/349 |

FOREIGN PATENT DOCUMENTS

EP 1148091 10/2001

OTHER PUBLICATIONS

Fry, Edward M., "Oxazoline Ring-Opening," J. Org. Chem., 15, pp. 802-806 (Jan. 16, 1950).
Mugesh, G. et al., "Synthesis and Structural Characterization of Monomeric Zing(II), Cadmium(II), and Mercury(II) Arenethiolates with a Chelating Oxazoline Ligand," European Journal of Inorganic Chemistry, No. 8, pp. 1229-1236 (1999).
Wiley, Richard H. et al., "The Chemistry of the Oxazolines," Chemical Reviews, vol. 44, pp. 447-476 (Apr. 3, 1949).
Yamamoto, Yoshinori et al., "The Influence of (Organo) Metallics 'Metal-Tuning' on Stereo- and Regio-Chemical Convergence in Reactions of Allylic Carbanions with Aldehydes," Journal of Organometallic Chemistry, vol. 292, pp. 311-318 (1985).
Hass, Christian, Apr. 1, 2011 European Search Report with Opinion from corresponding European Patent Application No. 06256596.5 (6 pp.).
Gong, Fangbin, English translation of May 5, 2011 Office Action from Chinese Patent Application No. 200710097690.7 [6 pp.].

* cited by examiner

*Primary Examiner* — Mark Eashoo
*Assistant Examiner* — Nicole M Buie-Hatcher

(57) ABSTRACT

Polymer-filler coupling compounds with the formula B-A-$S_x$—N are claimed. In these compounds, B is an azaheterocyclic oxygen or sulfur containing moiety, or an allyltin moiety; $S_x$ is a polysulfide, where x is between 2 and about 10; A is a linking atom or group that forms a bridge between B and $S_x$; and N is a blocking group. $S_x$ can be a disulfide. N can be a conventional blocking group or other group such as -A-B. Methods for using the polymer-filler coupling compounds to modify polymers containing unsaturated carbon-carbon bonds and promote filler dispersion are also claimed. Additionally, vulcanizable rubber compositions containing the polymer-filler coupling compounds and methods for making vulcanized rubber compositions using the polymer-filler coupling compounds are also claimed.

17 Claims, No Drawings

POLYMER-FILLER COUPLING ADDITIVES

CROSS-REFERENCE TO RELATED APPLICATION

This application claims priority from and is related to the following prior application: "Polymer-Filler Coupling Additives," U.S. Provisional Application No. 60/754,533, filed Dec. 28, 2005. This prior application, including the entirety of the written description and drawing figures, is hereby incorporated into the present application by reference.

FIELD

The technology described herein relates to compositions for coupling polymers and fillers, and polymer compositions including these coupling compositions.

BACKGROUND

The dispersion quality of fillers in polymeric compositions, i.e., the degree to which the filler is evenly distributed throughout a composition, can impact the performance properties of the polymeric compositions. One property that can be affected by the dispersion quality of a filler within a polymeric composition is hysteresis. The hysteresis of an elastomer, for example, refers to the difference between the energy applied to deform the elastomer and the energy recovered as the elastomer returns to its initial, undeformed shape. Interaction between elastomer molecules and an incorporated reinforcing filler or fillers is known to impact hysteresis.

Hysteresis and other physical properties of compounded elastomers can be improved by ensuring good dispersion of the filler throughout the polymer. When elastomeric compounds exhibiting good hysteresis are used in articles such as belts, tires, and the like, the articles demonstrate increased rebound and reduced heat build-up when subjected to mechanical stresses during use. In pneumatic tires, for example, lowered hysteresis values are associated with reduced rolling resistance and heat build-up during use. This reduction of rolling resistance and heat build-up in a pneumatic tire can result in lower fuel consumption for the vehicle using the tire.

SUMMARY

The polymer-filler coupling compounds described herein have the formula $B-A-S_x-N$. In these compounds, B is an azaheterocyclic oxygen or sulfur containing moiety, or an allyltin moiety; $S_x$ is a polysulfide, where x is between 2 and about 10; A is a linking atom or group that forms a bridge between B and $S_x$; and N is a blocking group. $S_x$ can be a disulfide. N can be a conventional blocking group or other group such as -A-B.

Methods for using the polymer-filler coupling compounds are also described herein. Methods for modifying a polymer involve contacting a polymer containing unsaturated carbon-carbon bonds in its molecular structure with a polymer-filler coupling compound. Methods for promoting filler dispersion in polymeric compositions involve reacting a polymer modified by a polymer-filler coupling compound with a filler that has a surface group that binds to the B moiety of the compound. The polymer-filler coupling compound, polymer, and filler can also be mixed together at the same time rather than sequentially to promote filler dispersion in a polymeric composition.

Vulcanizable rubber compositions containing the polymer-filler coupling compounds and methods for making vulcanized rubber compositions using the polymer-filler coupling compounds are also described herein. The vulcanizable rubber compositions include an elastomer containing unsaturated carbon-carbon bonds in its molecular structure, a hysteresis reducing amount of a polymer-filler coupling compound, a filler with a surface group that binds to the B moiety of the polymer-filler coupling compound, and a cure agent. The methods for making vulcanized elastomeric compositions involve mixing together a vulcanizable rubber composition as just described and curing the composition.

DETAILED DESCRIPTION

As examples of how a person of ordinary skill in the art can make and use the claimed invention, this description presents examples of compounds having the formula $B-A-S_x-N$, polymer compositions including these compounds, methods for using these compounds in polymer compositions, vulcanizable rubber compositions containing the polymer-filler coupling compounds, and methods for making vulcanized rubber compositions using the polymer-filler coupling compounds. This description is provided to meet the requirements of enablement and best mode without imposing limitations that are not recited in the claims.

Compounds with the formula $B-A-S_x-N$ are useful for promoting filler dispersion in a polymeric composition that comprises a polymer having unsaturated carbon-carbon bonds in its molecular structure. In these compounds with the formula $B-A-S_x-N$, B is an azaheterocyclic oxygen or sulfur containing moiety or an allyltin moiety; $S_x$ is a polysulfide, wherein x is between 2 and about 10; A is a linking atom or group that forms a bridge between B and $S_x$; and N is a blocking group.

When used in this specification, the term azaheterocyclic oxygen or sulfur containing moiety is intended to include the structures embodied by formulas I, II, and III:

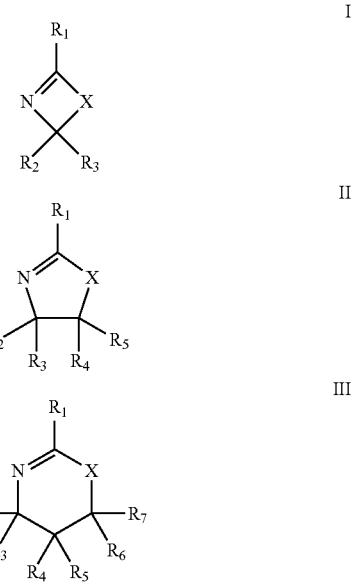

where X is oxygen or sulfur; and each of $R_1$, $R_2$, $R_3$, $R_4$, $R_5$, $R_6$, and $R_7$ is independently hydrogen, a branched or linear $C_1$-$C_{20}$ alkyl group, a branched or linear $C_3$-$C_{20}$ cycloalkyl group, a branched or linear $C_6$-$C_{20}$ aryl group, a branched or linear $C_7$-$C_{20}$ alkylaryl, or A, where A is a linking atom or group that forms a bridge between B and $S_x$. With respect to the R groups, each R group can be the same, e.g., hydrogen; each R group can be different, eg., two or more different groups; or some of the R groups can be the same while others are different, e.g., $R_1$ could be A, $R_2$ could be hydrogen, and the other R groups could be the same or different alkyl groups.

The allyltin moiety can comprise the formula —CH=CHCH$_2$Sn(R$_8$)$_3$, wherein $R_8$ is a branched or linear $C_1$-$C_{20}$ alkyl group, a branched or linear $C_3$-$C_{20}$ cycloalkyl group, a branched or linear $C_6$-$C_{20}$ aryl group, a branched or linear $C_7$-$C_{20}$ alkylaryl group, or mixtures thereof. The —CH portion of the allyltin moiety binds to the A group of the B-A-$S_x$—N compound to form (allyltin moiety)-A-$S_x$—N.

The linking atom or group A can be a branched or linear $C_1$-$C_{20}$ alkylenyl moiety, a branched or linear $C_3$-$C_{20}$ cycloalkylenyl moiety, a branched or linear $C_6$-$C_{20}$ arylenyl moiety, or a branched or linear $C_7$-$C_{20}$ alkylarylenyl moiety. Further, A can comprise [A'-(Z-A")$_k$], wherein A' and A" are a branched or linear $C_1$-$C_{20}$ alkylenyl moiety, a branched or linear $C_3$-$C_{20}$ cycloalkylenyl moiety, a branched or linear $C_6$-$C_{20}$ arylenyl moiety, or a branched or linear $C_7$-$C_{20}$alkylarylenyl moiety; Z is oxygen, sulfur or C=O; and k is 1 to about 4. For example, A can comprise a phenyl group with an ortho, meta, or para bond with B and/or $S_x$. As another example, A can comprise (CH$_2$)$_m$, where m is 1 to about 10.

The $S_x$ group is a polysulfide. The polysulfide can have two or more sulfur atoms. For example, the polysulfide can have between 2 and about 10 sulfur atoms, i.e., x is 2 to about 10. Generally, the more sulfur atoms that are present, the easier it is for the N group, a blocking group, to dissociate leaving a reactive B-A-$S_{y-1}$—S— molecule. The N group, upon dissociating, may have sulfur atoms still associated, i.e., the group that leaves can be —S—S$_{z-1}$—N. The y and z subscripts indicate the number of sulfur atoms associated with the respective disassociated molecules, where x=y+z.

The N group can be a conventional blocking group or other group including, for example, a B-A- group as described above (i.e., B-A-$S_x$-A-B). Additional examples of blocking groups include those groups known to be useful in blocking the sulfur portion of mercaptans. With these types of blocking groups, the mercapto hydrogen is replaced by another group that does not affect the reactivity of the organic portion of the mercaptan, i.e. in the case of a B-A-$S_x$—N molecule, the B moiety. Suitable mercapto blocking groups can include, but are not limited to, those described in U.S. Pat. Nos. 6,127, 468; 6,204,339; 6,528,673; 6,635,700; 6,649,684; and 6,683, 135, the disclosures of which are hereby incorporated by reference with respect to the mercapto blocking groups described. A deblocking agent can be added during the manufacturing process after the B-A-$S_x$—N reaction with the filler has occurred, to allow the sulfur atom of the B-A-$S_x$—N molecule to bond with the rubber. The deblocking agent can be added at any time during the compounding process as a single component during any mixing stage in which deblocking is desired. Often deblocking is desired after any mixing stage in which heat would be applied. The deblocking agent can be added during the cure stage of compounding and in the final mixing stage. The deblocking agent can be contained in a sulfur cure package arid, often, can function as a cure accelerator, especially in combination with a zinc salt. Examples of deblocking agent are well known to those skilled in the art.

One non-limiting example of a B-A-$S_x$—N compound is bis-[2-(2-oxazolinyl)-phenyl]-disulfide (2OPD), shown by formula IV:

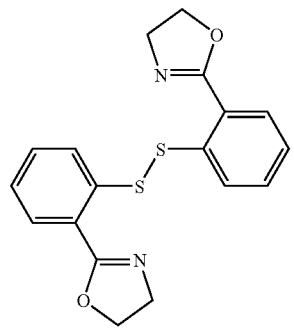

IV

Specifically, 2OPD is a B-A-$S_x$-A-B type molecule, where x is 2, i.e., N is -A-B and the A and B groups are the same on each side of the molecule. If B-A-$S_1$— is the group that leaves, then two identical molecules are formed of the structure shown by formula V:

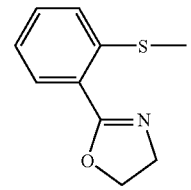

V

In B-A-$S_x$-A-B type molecules, the A moieties can be the same, as in the 2OPD molecule, or different. Similarly, in B-A-$S_x$-A-B type molecules the B moieties can be the same, as in the 2OPD molecule, or different. An additional non-limiting example of a B-A-$S_x$—N compound is bis-[2-(2-thiazolinyl)-phenyl]-disulfide (2TPD), shown by formula VI:

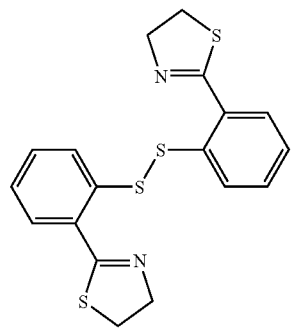

VI

Ordinary chemical synthesis methods can be used to produce the exemplary compounds and other B-A-$S_x$—N compounds without undue experimentation. An exemplary method for producing 2OPD is disclosed in Example A below. However, it is recognized that other known chemical synthesis methods, using other starting materials and intermediates, can also be used to produce these and other B-A-$S_x$—N compounds.

The polymers used herein contain carbon-carbon unsaturation in their molecular structure and include thermoplastic polymers as well as thermosetting polymers. The unsaturation can be present along the polymer backbone and/or can be present as a pendent group, such as an ethnic group and the like. Suitable elastomers containing carbon-carbon unsaturation in their molecular structure include natural as well as synthetic rubbers, such as those produced by polymerizing aliphatic, conjugated diolefins, especially those containing 4 to 8 carbon atoms per molecule such as, but not limited to, butadiene, isoprene, pentadienes, and the like, or the copolymers and terpolymers of such dienes. The polymer backbones of the elastomers used herein can contain a significant amount of unsaturation. As an example, at least about 5% of the carbon-carbon bonds in the polymer backbones are unsaturated bonds.

Characterization of rubber as having unsaturated carbon chains is well known in the art as shown by ANSI/ASTM Standard D 1418-79A where unsaturated-chain rubbers are referred to as R rubbers. Class R rubbers include natural rubber and various synthetic rubbers derived at least partly from diolefins. The following is a non-exclusive list of R class rubbers that can be used in the compositions of the present invention: acrylate-butadiene rubber; butadiene rubber; chloro-isobutene-isoprene rubber; chloroprene rubber; synthetic isoprene; nitrile-butadiene rubber; nitrile-chloroprene rubber; nitrile-isoprene rubber; natural rubber; styrene-butadiene rubber; styrene-chloroprene rubber; and styrene-isoprene rubbers. The rubbers used herein having carbon-carbon unsaturation also can be other than the R rubbers such as, but not limited to EPDM rubber derived from ethylene-propylenediene monomer, and typically having about 3% to about 8% of their carbon bonds as unsaturated carbon-carbon bonds.

Further examples of synthetic polymers that can be used in the compositions disclosed herein include, but are not limited to, the homopolymerization products of butadiene and its homologues and derivatives such as, for example, methyl butadiene, dimethyl butadiene and pentadienes as well as copolymers formed from a butadiene or its homologues or derivatives with other unsaturated organic compounds. Among the latter are olefins, for example, ethylene, propylene or isobutylene which copolymerize with isoprene to form polyisobutylene also known as butyl rubber; vinyl compounds that can copolymerize with diene monomers such as butadiene and isoprene; acrylic acid, acrylonitrile, methacrylonitrile, methacrylic acid, alpha methyl styrene, (o-, m-, or p-) methyl styrene and styrene, the latter compound polymerizing with butadiene to form styrene-butadiene rubber, as well as vinyl esters and various unsaturated aldehydes, ketones and ethers, such as acrolein and vinylethyl ether, and the like.

In general, examples of the elastomers for use with the compositions include homopolymers of conjugated diene monomers, and copolymers and terpolymers of the conjugated diene monomers with monovinyl aromatic monomers and trienes. More specifically, examples of elastomers for use with the compositions include natural rubber, synthetic polyisoprene, polybutadiene, polystyrene, styrene-butadiene copolymers, isoprene-butadiene copolymers, isoprene-styrene copolymers, terpolymers of styrene-isoprene-butadiene, acrylonitrile-butadiene rubber, terpolymers of acrylonitrile, butadiene, styrene, and blends thereof.

The chemical reaction between the B-A-S$_x$—N compounds and a polymer that contains unsaturated carbon-carbon bonds in its molecular structure is illustrated in Scheme 1. In Scheme 1, the polymer (P) is represented as having "n" repeating units that can react with "n" moles of B-A-S$_x$—N. From a practical standpoint, it is recognized that not all available reaction sites in the polymeric molecular structure will react and, therefore, "n" is meant to represent an average number of reactive sites. For convenience, the modified polymer produced in Scheme 1 is illustrated as P—(S$_y$-A-B)$_n$. As discussed above the "y" designation indicates the number of sulfur atoms associated with the molecule after the —S$_z$—N group leaves, where x=z+y.

Schemes 2-9 illustrate the other reaction, i.e., the binding of the B moiety of the P—(S$_y$-A-B)$_n$ compound to a reactive group on the surface of a filler. The discussion here uses the reaction product from Scheme 1 including the polymer. The reaction of the B moiety, however, occurs independently of the reaction of the B-A-S$_x$—N compound with a polymer. That is, it is not necessary for the B-A-S$_x$—N compound to be bound to a polymer in order for the B moiety-filler reaction to occur. The B moiety-filler reaction can occur prior to, at the same time as, or after the B-A-S$_x$—N compound is coupled to the polymer.

As illustrated in Schemes 2-9, a B moiety can comprise an azaheterocyclic oxygen or sulfur containing moiety that is reactive with surface groups of carbon black (CB), such that mixing P—(S$_y$-A-B)$_n$ with the carbon black allows for the direct binding of carbon black to a B moiety of the compound. Thus, the filler is bound along the molecular structure of the polymer by the reaction of B with the polymer.

Scheme 10 illustrates a reaction where a B moiety of P—(S$_y$-A-B)$_n$ can comprise an allyltin group that is reactive with the surface ortho-quinone structures present on carbon black, such that mixing P—(S$_y$-A-B)$_n$ with carbon black filler allows for the direct binding of carbon black to the B moiety of the P—(S$_y$-A-B)$_n$ compound and the binding of the carbon black filler along with the molecular structure of the polymer by the reaction of B with the polymer.

Scheme 1

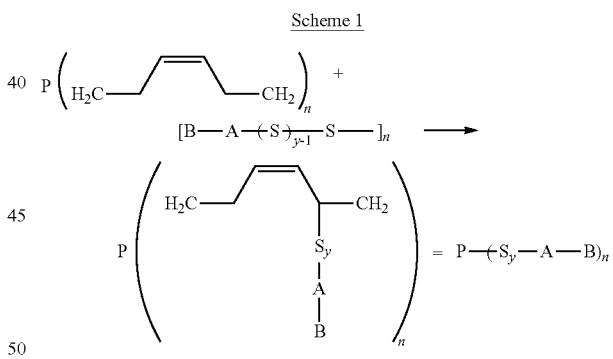

Scheme 2

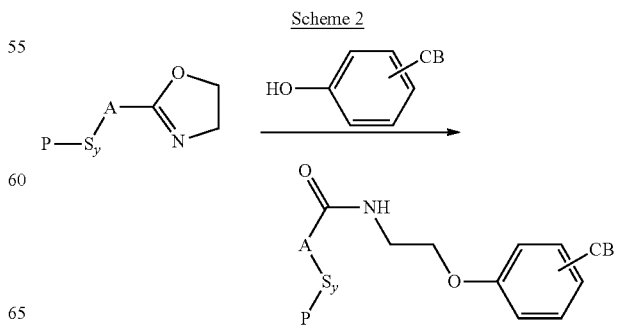

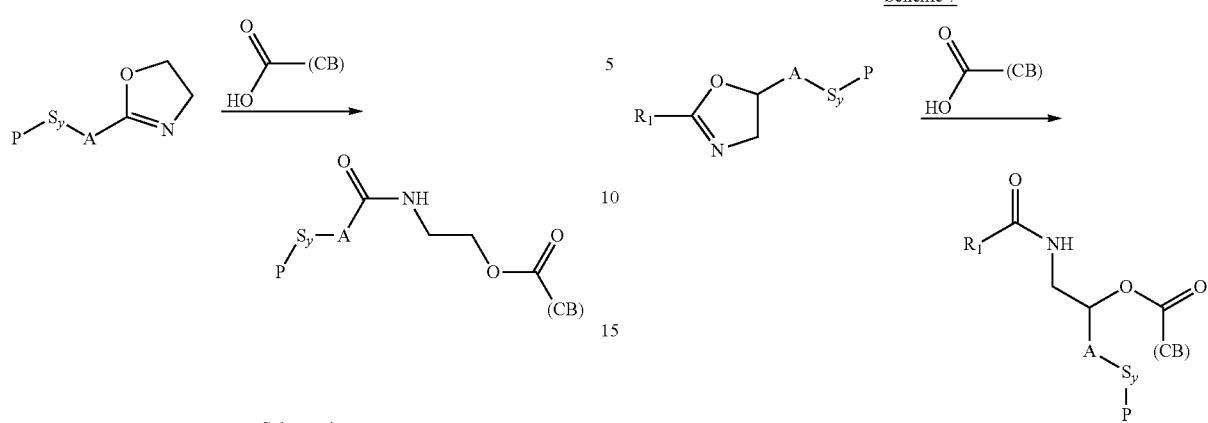
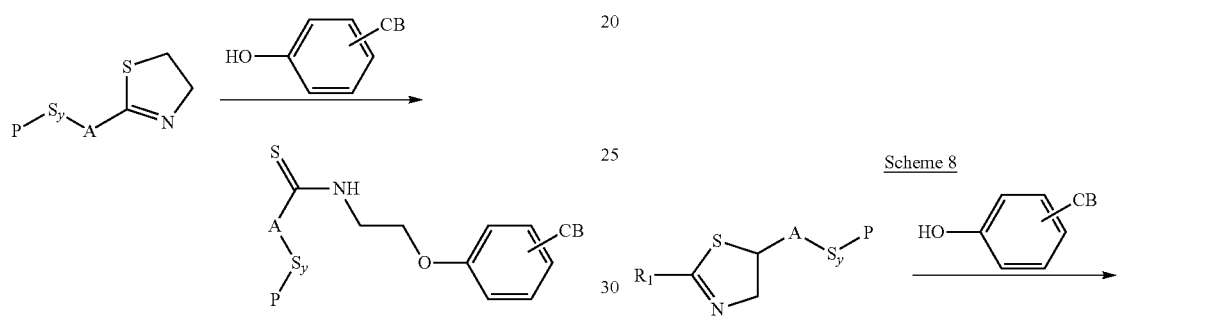
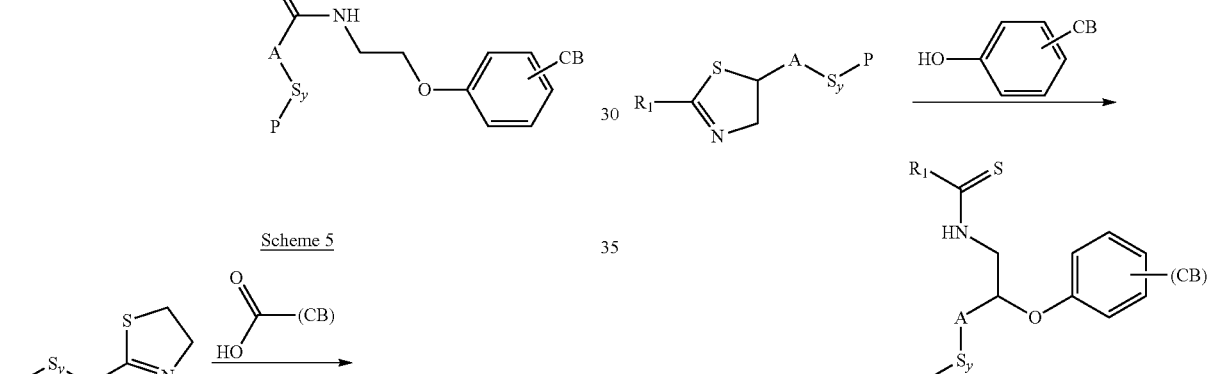
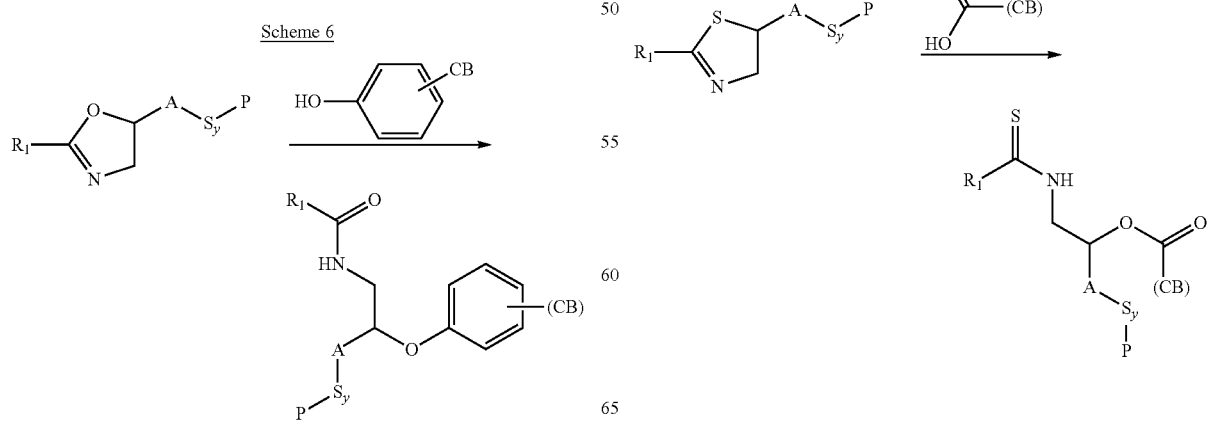

Scheme 10

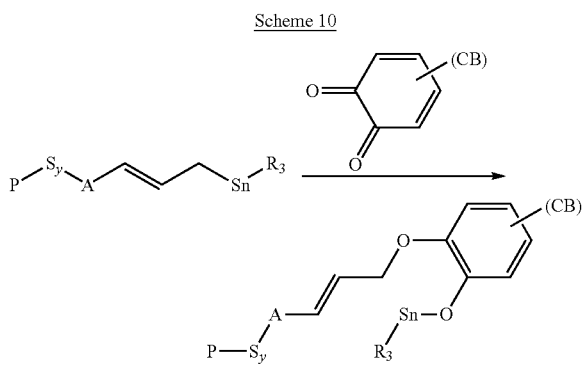

In each of the reactions illustrated by Schemes 2-10, more than one B-A-$S_x$—N molecule can be bound to a carbon black filler particle or aggregate if multiple reactive groups are present on the filler particle or aggregate. Further, other fillers with surface groups reactive with the B moiety of B-A-$S_x$—N can be mixed with carbon black and bound along the molecular structure of the polymer by the reaction of B with the polymer. For example, mineral fillers such as, but not limited to, silica, talc, kaolin, clay, metal oxides, aluminum hydrate, mica, and the like, have such reactive surface groups, and these fillers can be employed in mixtures containing carbon black.

As illustrated in Scheme 1 above, a modified polymer can be produced by contacting a polymer containing unsaturated carbon-carbon bonds in its molecular structure with a compound having the formula B-A-$S_x$—N, as described above, to form a modified polymer. The amount of the B-A-$S_x$—N compound can range from about 0.1 to about 30 percent by weight calculated on the weight of the polymer to be modified. Alternatively, the amount of the B-A-$S_x$—N compound can range from about 0.5 to about 10 percent by weight of the polymer. Additionally, the amount of the B-A-$S_x$—N compound can range from about 1 to about 8 percent by weight of the polymer. The modification reaction can be conducted in solution, or under solvent-free conditions (solid state reaction). The B-A-$S_x$—N compound can be added to the rubbers by any conventional technique, such as milling or in a Banbury mixer.

For example, a modified polymer can be obtained at any time after polymerization, such as by addition of the B-A-$S_x$—N compound to the cement obtained from polymerization, by spraying the compound onto the dried polymer crumb or by adding the compound to a polymeric composition with the polymer prior to or at the same time as adding the filler.

Thus, a method for promoting filler dispersion in a polymeric composition can comprise the steps of: (a) modifying a polymer having unsaturated carbon-carbon bonds in its molecular structure by reacting the polymer with a compound having the formula B-A-$S_x$—N to form a modified polymer, and (b) reacting the modified polymer with a filler comprising a surface group that can bind to the B moiety of the compound.

In another example, a method for promoting filler dispersion in a polymeric composition can comprise the step of mixing together (i) a polymer having unsaturated carbon-carbon bonds in its molecular structure, (ii) a compound having the formula B-A-$S_x$—N; and (iii) a filler comprising a surface group that can bind to the B moiety of the compound.

Vulcanizable elastomeric compositions according to the invention comprise an elastomer containing unsaturated carbon-carbon bonds in its molecular structure; a hysteresis-reducing amount of a compound having the formula B-A-$S_x$—N, e.g., about 0.1 to about 30 percent by weight of the elastomer; a filler comprising a surface group that can bind to the B moiety of the compound; and a cure agent. The term cure agent as used herein means a cure package containing sulfur and accelerators commonly used in sulfur-vulcanizable rubber compositions. The filler is carbon black or a mixture of carbon black with another filler having a surface group that can bind to the B moiety of the compound. In one example, the B-A-$S_x$—N compound is added in the masterbatch containing the elastomer and the filler. In another example, the B-A-$S_x$—N compound can be pre-reacted with the elastomer to form a modified elastomer, as described above. In yet another example, the B-A-$S_x$—N compound can be reacted with the elastomer and the filler by adding it in a remill stage or final mixing stage.

Thus, a method for making a vulcanized elastomeric composition can comprise the steps of (a) mixing together (i) an elastomer containing unsaturated carbon-carbon bonds in its molecular structure, (ii) a compound having the formula B-A-$S_x$—N, (iii) a filler comprising a surface group that can bind to the B moiety of the compound, and (iv) a cure agent; and (b) curing the composition.

A method for making a vulcanized elastomeric composition can comprise the steps of: (a) mixing together (i) a modified elastomer prepared by reacting an elastomer having unsaturated carbon-carbon bonds in its molecular structure with a compound having the formula B-A-$S_x$—N, (ii) a filler comprising a surface group that can bind to the B moiety of the compound, and (iii) a cure agent; and (b) curing the composition.

The resulting vulcanizable elastomeric composition, after both the S-polymer and B-filler reactions have occurred, comprises (a) the reaction product of (i) an elastomer having unsaturated carbon-carbon bonds in its molecular structure, (ii) a compound having the formula B-A-$S_x$—N, and (iii) a filler comprising a surface group bound to the B moiety of the compound; and (b) a cure agent.

The conjugated diene polymers, or copolymers or terpolymers of conjugated diene monomers and monovinyl aromatic monomers, can be utilized as 100 parts of the rubber in a treadstock compound, or they can be blended with any conventionally employed treadstock rubber which includes natural rubber, synthetic rubber and blends thereof. Such rubbers are well known to those skilled in the art and include, but are not limited to, acrylonitrile-butadiene rubber, silicone rubber, the fluoroelastomers, ethylene acrylic rubber, ethylene vinyl acetate copolymer, epichlorohydrin rubbers, chlorinated polyethylene rubbers, chlorosulfonated polyethylene rubbers, hydrogenated nitrile rubber, tetrafluoroethylene-propylene rubber and the like. When the vulcanizable elastomeric composition of the present invention is blended with conventional rubbers, the amounts can vary widely with a lower limit comprising about ten percent to 20 percent by weight of the total rubber. The minimum amount will depend primarily upon the physical properties desired.

The vulcanizable elastomeric composition can be compounded with reinforcing fillers, such as carbon black or a mixture of carbon black and another filler. Any form of carbon black can be used. The carbon black can be present in amounts ranging from about 0 phr to about 100 phr. Alternatively, carbon black can be compounded at about 5 to about 80 phr and, additionally, an amount from about 20 to about 70 phr can be used. The carbon blacks can include any of the commonly available, commercially-produced carbon blacks. For example, carbon blacks having a surface area of at least about 20 m²/g up to about 200 m²/g and, additionally, carbon blacks having surface areas of at least about 35 m²/g up to about 200 m²/g can also be used. Surface area values are those determined by ASTM test D-1765 using the cetyltrimethylammonium bromide (CTAB) technique.

Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks that can be used include acetylene blacks. Typical carbon blacks that are used include N110, N121, N220, N231, N242, N293, N299, N326, N330, N332, N339, N343, N347, N351, N358, N375, N472, N539, N472, N539, N550, N660, N683, N754, and N765. Oxidized carbon blacks can also be used. The carbon blacks can be oxidized using any suitable conventional technique such as oxidation by ozone, dichromate, or oxidizing acids. For example, carbon blacks oxidized using nitrogenous oxidizing acids or ozone can be used. Examples of suitable methods of producing oxidized carbon blacks are disclosed in U.S. Pat. Nos. 3,914,148; 4,075,140; and 4,075,157 which are hereby incorporated by reference. Depending on the particular use of the compound, the appropriate carbon black can be selected. Mixtures of two or more of the above blacks can be used in preparing products of this invention. The carbon blacks utilized in the preparation of the filled vulcanizates of the invention can be in pelletized form or an unpelletized flocculant mass. Unpelletized carbon black can be employed to aid in achieving uniform mixing.

The vulcanizable elastomeric compositions can also contain additional processing additives and conventional rubber additives including, for example, additional fillers, plasticizers, antioxidants, activators, retarders, accelerators, pigments, cure agents, processing additives such as oils and resins, including tackifying resins, pigments, fatty acid, zinc oxide, waxes, antioxidants, anti-ozonants, and peptizing agents. As known to those skilled in the art, depending on the intended use of the sulfur vulcanizable and sulfur vulcanized material (rubbers), the additives mentioned above are selected and commonly used in conventional amounts, using standard rubber mixing equipment and procedures. Such elastomeric compositions, when vulcanized using conventional rubber vulcanization conditions, exhibit reduced hysteresis, which means a product having increased rebound, decreased rolling resistance and lessened heat build-up when subjected to mechanical stress. Products including tires, power belts and the like are envisioned. Decreased rolling resistance is, of course, a useful property for pneumatic tires, both radial as well as bias ply types and thus, the vulcanizable elastomeric compositions of the present invention can be utilized to form treadstocks for such tires. Pneumatic tires can be made according to the constructions disclosed in U.S. Pat. Nos. 5,866,171; 5,876,527; 5,931,211; and 5,971,046, the disclosures of which are incorporated herein by reference. The composition can also be used to form other elastomeric tire components such as subtreads, sidewalls, body ply skims, bead fillers and the like.

Thus, examples include vulcanizates of the vulcanizable rubber compositions described above, and a tire comprising at least one component that comprises a vulcanized elastomeric composition that comprises the reaction product of an elastomer having unsaturated carbon-carbon bonds in its molecular structure, a filler comprising carbon black or mixtures of carbon black and other fillers, a cure agent, and a compound having the formula $B-A-S_x-N$. For example, the tire component can be a tire tread.

Typical amounts of tackifier resins, if used, comprise about 0.5 to about 10 phr, usually about one to about 5 phr. Typical amounts of compounding aids comprise about one to about 50 phr. Such compounding aids can include, for example, aromatic, naphthenic, and/or paraffinic processing oils.

Representative of the antidegradants that can be in the rubber composition include monophenols, bisphenols, thiobisphenols, polyphenols, hydroquinone derivatives, phosphates, phosphate blends, thioesters, naphthylamines, diphenol amines as well as other diaryl amine derivatives, paraphenylene diamines, quinolines and blended amines. Antidegradants are generally used in an amount ranging from about 0.1 phr to about 10 phr. Alternatively, antidegradants can be used in a range of from about 0.5 to 6 phr. For example, typical amounts of antioxidants comprise about 0.1 to about 5 phr. Representative antioxidants can be, for example diphenyl-p-phenylenediamine and others, such as for example, those disclosed in the *Vanderbilt Rubber Handbook* (1978), pages 344 to 346. Typical amounts of anti-ozonants can comprise about 0.1 to about 5 phr.

Typical amounts of fatty acids, if used, which can include stearic acid, palmitic acid, linoleic acid or a mixture of one or more fatty acids, can comprise about 0.5 to about 3 phr. Typical amounts of waxes comprise about one to about 2 phr. Often microcrystalline waxes are used. Typical amounts of peptizers, if used, comprise about 0.1 to about 1 phr. Typical peptizers can be, for example, pentachlorothiophenol and dibenzamidodiphenyl disulfide. Pentachlorophenol can be used, for example, in an amount ranging from about 0.1 phr to 0.4 phr. Alternatively, pentachlorophenol can be used in a range of from about 0.2 to 0.3 phr.

Representative of processing oils which can be used in the rubber composition of the present invention include Black Oil (a naphthenic oil with additives having polycyclic aromatic content of less than 3%, sold under this designation by Ergon), aliphatic-naphthenic aromatic resins, polyethylene glycol, petroleum oils, ester plasticizers, vulcanized vegetable oils, pine tar, phenolic resins, petroleum resins, polymeric esters and resins. These processing oils can be used in a conventional amount ranging from about 0 to about 50 phr. Alternatively, the processing oils can be used in a range of from about 5 to 25 phr.

It is readily understood by those having skill in the art that the rubber composition would be compounded by methods generally known in the rubber compounding art, such as mixing the various vulcanizable polymer(s) with various commonly used additive materials such as, for example, curing agents, activators, retarders, accelerators, and the like.

The reinforced rubber compounds can be cured in a conventional manner with known vulcanizing agents, such as such as sulfur and accelerators. Modification of polymers and filler binding according to the present invention does not appreciably affect cure times and, thus, the rubber compounds can be cured for a conventional amount of time. When a vulcanizing agent is used, the amount of the agent used is 0.1 to 5 parts by weight, based on 100 parts by weight of the rubber material. Alternatively, the amount of the vulcanizing agent used can be 0.1 to 3 parts by weight, based on 100 parts by weight of the rubber material, and, additionally, a range of from about 0.1 phr to about 2 phr can be used. Vulcanizing agents can be used alone or in combination. Cured or crosslinked polymers will be referred to as vulcanizates for purposes of this disclosure. For a general disclosure of suitable vulcanizing agents, one can refer to Kirk-Othmer, *Encyclopedia of Chemical Technology*, 3rd ed., Wiley Interscience, N.Y. 1982, Vol. 20, pp. 365 to 468, particularly "Vulcanization Agents and Auxiliary Materials," pp. 390 to 402.

Zinc oxide and stearic acid are conventionally used to vulcanize elastomers. Zinc oxide is generally used in a conventional amount ranging from about 0.5 to about 5 phr. Stearic acid is generally used in a conventional amount ranging from about 1 to about 4 phr.

The vulcanization is conducted in the presence of a sulfur vulcanizing agent. Examples of suitable sulfur vulcanizing agents include "rubbermaker's" soluble sulfur; sulfur donating vulcanizing agents, such as an amine disulfide, polymeric polysulfide or sulfur olefin adducts; and insoluble polymeric sulfur. The sulfur vulcanizing agents can be a mixture of soluble and insoluble polymeric sulfur. The sulfur vulcanizing agents are used in an amount ranging from about 0.1 to about 10 phr. Alternatively, the sulfur vulcanizing agents can be used in an amount ranging from about 1.5 to about 5 phr, and, additionally, the sulfur vulcanizing agents can range from about 1.5 to about 3.5 phr.

Accelerators are used to control the time and/or temperature required for vulcanization and to improve properties of the vulcanizate. The vulcanization accelerators used in the present invention are not particularly limited. Representative of conventional accelerators are amines, guanidines, thioureas, thiols, thiurams, sulfenamides, dithiocarbamates and xanthates. Additional examples include thiazole vulcanization accelerators, such as 2-mercaptobenzothiazole, benzothiazole disulfide, N-cyclohexyl-2-benzothiazole sulfenamide (CBS), N-tert-2-benzothiazole sulfenamide (TBBS), and the like; and guanidine vulcanization accelerators, such as diphenylguanidine (DPG) and the like. The amount of vulcanization accelerator used can be about 0.1 to about 10 phr. Alternatively, vulcanization accelerators can be added in amounts ranging from about 0.1 phr to about at 5 phr, or about 0.2 to about 3 phr.

The vulcanizable elastomeric composition of the present invention can be obtained by milling the components by using a milling apparatus, such as a mill, an internal mixer, and the like for a sufficient time and at a high enough temperature to achieve the desired physical properties of the resulting compound. The mixing of the vulcanizable elastomeric composition can be accomplished by methods known to those having skill in the rubber mixing art. For example, the ingredients can be mixed in two or more stages, consisting of at least a "master batch" stage (comprising mixing of the elastomer, with at least a portion of the carbon black and/or silica and other ingredients); and a "final stage", in which the cure agents are typically added. There can also be a mixing stage in which the mixture is re-milled without the addition of ingredients. The B-A-$S_x$—N compound can be added in any stage of the mixing process, The mixing temperature can vary from stage to stage. However, for purposes of the examples disclosed herein, the B-A-$S_x$—N compound, the elastomer, and the filler can be mixed at a mixing temperature of about 60° C. to about 200° C. Alternatively, the elastomer and the filler can be mixed at a mixing temperature of about 90° C. to about 190° C. and, additionally, about 120° C. to about 180° C. In one example, a portion of the filler and/or the B-A-$S_x$—N compound can be added to the elastomer in the master batch stage, and the remainder added to a remill stage.

EXAMPLES

The following examples illustrate the preparation of an exemplary B-A-$S_x$—N compound and elastomeric compositions containing the compound. These examples are not intended to be limiting, as other methods for preparing the compound and the rubber compositions and different rubber compounding compositions can be employed without departing from the scope of the claims set forth below.

Example A

Synthesis of bis-[2-(2-oxazolinly)-phenyl]-disulfide (2OPD)

A mixture of 20 g of 2,2'-dithio-bis-(benzoic acid) (65 mmol) in 28.6 mL thionylchloride (390 mmol) was refluxed for 12 hours and then filtered. The filtrate was dried using a rotary evaporator and 15.0 g of 2,2'-dithio-bis-(benzoyl chloride) powder (44 mmol) was collected. Yield for this reaction was 68%.

The 2,2'-dithio-bis-(benzoyl chloride) was then mixed into 300 mL of chloroform. To this mixture a solution maintained at OC comprising 10.7 g 2-aminoethanol (175 mmol) in 200 mL choloroform was added dropwise with stirring. Upon completion of the addition, the resulting mixture was stirred at 25° C. for 2 hours during which a precipitate formed. The precipitate was collected with filtration and washed with 200 mL of water. The precipitate was then dried yielding a light brown powder. 13.5 g of 2,2'-dithio-bis-[N-(hydroxyethyl)-benzamide] (34 mmol) was collected providing a 77% yield.

15 mL of thionylchloride (204 mmol) was then added dropwise with stirring to the 2,2'-dithio-bis-[N-(hydroxyethyl)-benzamide] powder. This mixture was poured into 150 mL of ether and a white precipitate formed. The precipitate was then filtered and dissolved in water. The dissolved precipitate was then neutralized with cold 20% sodium hydroxide and extracted with chloroform. The chloroform extract was dried and recrystallized with hexane. 7 g of bis-[2-(2-oxazolinyl)-phenyl]-disulfide (20 mmol) was collected providing a 59% yield. The overall yield for the synthesis was 15%.

Example B

To determine the effect of 2OPD on the hysteresis properties of rubber, four rubber compounding compositions containing solution SBR, carbon black, and other typical compounding ingredients were prepared. As shown in Table 1, a control composition (C1), two compositions containing 2OPD (E1 and E2), and a comparison composition (C2) containing a commercially available additive (Sumifine® 1162, available from Sumitomo Chemical Company) known to reduce hysteresis in natural rubber were prepared.

TABLE 1

Compounding Formulations

| | Composition[a] | | | |
|---|---|---|---|---|
| | C1 | E1 | E2 | C2 |
| Masterbatch | | | | |
| Polymer[b] | 100 | 100 | 100 | 100 |
| Carbon Black[c] | 50 | 50 | 50 | 50 |
| Aromatic Oil | 15 | 15 | 15 | 15 |
| Stearic Acid | 2 | 2 | 2 | 2 |
| 6PPD[d] | 1 | 1 | 1 | 1 |
| 2OPD | — | 1.42[e] | 2.84[f] | — |
| Sumifine 1162 | — | — | — | 2.55[g] |
| Final | | | | |
| ZnO | 3.0 | 3.0 | 3.0 | 3.0 |

TABLE 1-continued

Compounding Formulations

| | Composition[a] | | | |
|---|---|---|---|---|
| | C1 | E1 | E2 | C2 |
| DPG[h] | 0.5 | 0.5 | 0.5 | 0.5 |
| TBBS[i] | 1.0 | 1.0 | 1.0 | 1.0 |
| Sulfur | 1.3 | 1.3 | 1.3 | 1.3 |

[a]phr
[b]Solution SBR 35% styrene, 14% Vinyl, 20 phr of aromatic oil
[c]N339
[d]N-(1,3-dimethylbutyl)-N'-phenyl-1,4-benzenediamine (antioxidant)
[e]4 mmol
[f]8 mmol
[g]8 mmol
[h]diphenylguanidine (DPG)
[i]N-tert-2-benzothiazole sulfenamide (TBBS)

To determine the properties of the compositions in Table 1, several tests were run including Mooney Viscosity; tensile properties; and strain, including tan delta (tan δ), loss modulus (G'), and Payne effect (ΔG'). Test results are shown in Table 2. The Mooney Viscosity measurement (measured prior to annealing) was conducted at 130° C. using a large rotor, and was recorded as the torque when the rotor had rotated for four minutes. The sample was preheated at 130° C. for one minute before the rotor was started. The tensile properties for cured stock were measured using the standard procedure described in ASTM-D 412 at room temperature and 100° C. The tensile test specimens were rings with a diameter of 1.3 mm and a thickness of 1.9 mm. A gauge length of 25.4 mm was used for calculating the tensile properties. To determine if hysteresis was reduced, tan δ and G' at 5% strain and ΔG' at 0.1 to 20% strain using an ARES-A rheometer at 50° C. and 15 Hz were measured. Tan δ and G' were also measured during a temperature ramp at a constant 2% strain and 15 Hz (values for 25° C., 50° C., and 75° C. are shown in Table 2).

TABLE 2

Comparison of Composition Properties

| | Composition[a] | | | |
|---|---|---|---|---|
| | C1 | E1 | E2 | C2 |
| Mooney Viscosity | | | | |
| ML1 + 4/130° C. | 47 | 44 | 42 | 108 |
| Ring Tensile @ RT | | | | |
| M50 (MPa) | 1.30 | 1.58 | 1.89 | 1.38 |
| M300 (MPa) | 9.51 | 12.65 | 15.25 | 8.20 |
| TB (MPa) | 18.93 | 17.81 | 16.00 | 17.60 |
| EB (%) | 499 | 391 | 315 | 532 |
| Ring Tensile @ 100° C. | | | | |
| M50 (MPa) | 0.95 | 1.22 | 1.45 | 0.99 |
| M300 (MPa) | 4.00 | 5.84 | 7.45 | 3.58 |
| TB (MPa) | 9.85 | 7.54 | 7.79 | 8.83 |
| EB (%) | 375 | 238 | 207 | 361 |
| Strain Sweep (50° C., 15 Hz) | | | | |
| 5.0% strain G' (MPa) | 2.84 | 3.50 | 3.99 | 3.82 |
| tan δ | 0.211 | 0.206 | 0.189 | 0.200 |
| ΔG' [0.1-20% strain] (MPa) | 2.898 | 3.940 | 4.200 | 4.422 |
| Temp Ramp (2% strain, 15 Hz) | | | | |
| 25° C. G' (MPa) | 5.11 | 6.33 | 7.37 | 6.66 |
| tan δ | 0.229 | 0.196 | 0.176 | 0.202 |

TABLE 2-continued

Comparison of Composition Properties

| | Composition[a] | | | |
|---|---|---|---|---|
| | C1 | E1 | E2 | C2 |
| 50° C. G' (MPa) | 3.82 | 4.92 | 5.87 | 5.15 |
| tan δ | 0.191 | 0.164 | 0.145 | 0.176 |
| 75° C. G' (MPa) | 3.17 | 4.04 | 4.86 | 4.31 |
| tan δ | 0.166 | 0.160 | 0.155 | 0.170 |

Tan δ is a measure of the ratio of the loss of modulus of the composition to the storage modulus and it has been found that the lower the magnitude of tan δ at 50° C., the lower the hysteresis of the composition. As can be seen by the results listed in Table 2, the rubbers compounded with 2OPD showed reduced Mooney Viscosity values, similar ring tensile values (both at room temperature and 100° C.), and lower hysteresis (lower tan δ) compared to the C1 and C2 compositions. Improved Mooney Viscosity indicates improved processability. Similar ring tensile values for the rubbers compounded with 2OPD indicate the compositions have similar mechanical strengths. Lower tan δ values at 50° C. for the rubbers compounded with 2OPD indicate improved rolling resistance in tire treads made from these compositions.

In summary, the addition of an exemplary B-A-$S_x$—N compound, 2OPD, to rubber compositions resulted in lowered hysteresis indicating improved rolling resistance in tire treads made using B-A-$S_x$—N compounds.

This written description uses examples to disclose the invention, including the best mode, and also to enable a person skilled in the art to make and use the invention. The patentable scope of the invention is defined by the claims, and may include other examples that occur to those skilled in the art. Such other examples, which may be available either before or after the application filing date, are intended to be within the scope of the claims if they have elements that do not differ from the literal language of the claims, or if they include equivalent elements with insubstantial differences from the literal language of the claims.

We claim:

1. A compound having the formula B-A-$S_x$—N, wherein:
B is an azaheterocyclic oxygen or sulfur containing moiety, or an allyltin moiety;
$S_x$ is a polysulfide, where x is between 2 and about 10; and
N is a blocking group;
wherein the azaheterocyclic oxygen or sulfur containing moiety is selected from the group consisting of formulas I-III:

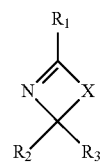

I

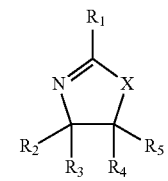

II

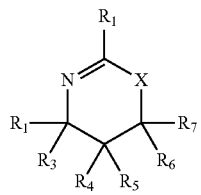

wherein X is oxygen or sulfur; wherein each of $R_1$, $R_2$, $R_3$, $R_4$, $R_5$, $R_6$, and $R_7$ is independently hydrogen, a branched or linear $C_1$-$C_{20}$ alkyl group, a branched or linear $C_3$-$C_{20}$ cycloalkyl group, a branched or linear $C_6$-$C_{20}$ aryl group, a branched or linear $C_7$-$C_{20}$ alkylaryl group, and A, wherein A comprises $[A'-(Z-A'')_k]$, wherein A' and A'' are a branched or linear $C_1$-$C_{20}$ alkylenyl moiety, a branched or linear $C_3$-$C_{20}$ cycloalkylenyl moiety, a branched or linear $C_6$-$C_{20}$ arylenyl moiety, or a branched or linear $C_7$-$C_{20}$ alkylarylenyl moiety; Z is oxygen, sulfur or C=O; and k is 1 to about 4.

2. A compound having the formula B-A-$S_x$—N promoting filler dispersion in composition comprising a polymer containing unsaturated carbon-carbon bonds in its molecular structure and a filler having a surface group reactive with B, wherein the filler is carbon black or carbon black and a mineral filler; B is an azaheterocyclic oxygen or sulfur containing moiety, or an allyltin moiety; $S_x$ is a polysulfide, where x is between 2 and about 10; and N is a blocking group, wherein A comprises $[A'-(Z-A'')_k]$, wherein A' and A'' are a branched or linear $C_1$-$C_{20}$ alkylenyl moiety, a branched or linear $C_3$-$C_{20}$ cycloalkylenyl moiety, a branched or linear $C_6$-$C_{20}$ arylenyl moiety, or a branched or linear $C_7$-$C_{20}$ alkylarylenyl moiety; Z is oxygen, sulfur or C=O; and k is 1 to about 4.

3. A method for modifyng a polymer comprising contacting a polymer containing unsaturated carbon-carbon bonds in its molecular structure with bis bis-[2-(2-oxazolinyl)-phenyl]-disulfide.

4. A method for promoting filler dispersion in a polymeric composition, comprising the steps of:
modifying a polymer comprising contacting a polymer containing unsaturated carboncarbon bonds in its molecular structure with bis-[2-(2-oxazolinyl)-phenyl]-disulfide to form a modified polymer; and reacting the modified polymer with a filler comprising a surface group that binds to the B moiety of the compound, wherein the filler is carbon black or carbon black and a mineral filler.

5. A method for promoting filler dispersion in a polymeric composition, comprising mixing together (i) a polymer having unsaturated carbon-carbon bonds in its molecular structure; (ii) a compound having the formula B-A-$S_x$-N, wherein B is an azaheterocyclic oxygen or sulfur containing moiety, or an allyltin moiety; S, comprises a polysulfide, wherein x is 2 to about 10; A is a linking atom or group that forms a bridge between B and S and N is a blocking group; and (iii) a filler having a surface group that binds to the B moiety of the compound, wherein the filler is carbon black or a mixture of carbon black and a mineral filler.

6. The method of claim 5, wherein the amount of the compound having the formula B-A-$S_x$—N is about 0.1 percent to about 30 percent by weight of the elastomer.

7. The method of claim 5, wherein the compound is bis-[2-(2-oxazolinyl)-phenyl]-disulfide.

8. The method of claim 5, wherein the mineral filler is silica, talc, kaolin, clay, metal oxides, aluminum hydrate, mica, or mixtures thereof.

9. A vulcanizable rubber composition, comprising:
(a) an elastomer containing unsaturated carbon-carbon bonds in its molecular structure;
(b) a hysteresis-reducing amount of a compound having the formula B-A-$S_x$—N, wherein B is an azaheterocyclic oxygen or sulfur containing moiety, or an allyltin moiety; $S_x$ comprises a polysulfide, wherein x is 2 to about 10; A is a linking atom or group that forms a bridge between B and $S_x$; and N is a blocking group;
(c) a filler comprising a surface group that binds to the B moiety of the compound, wherein the filler is carbon black or carbon black and a mineral filler; and
(d) a cure agent.

10. The composition of claim 9, wherein the hysteresis reducing amount of the compound having the formula B-A-$S_x$—N is about 0.1 percent to about 30 percent by weight of the elastomer.

11. The composition of claim 9, wherein the elastomer is a homopolymer of a conjugated diene monomer, or a copolymer or terpolymer of a conjugated diene monomer with a monovinyl aromatic monomer or a triene.

12. The composition of claim 11, wherein the elastomer is natural rubber, synthetic polyisoprene, polybutadiene, polystyrene, styrene-butadiene copolymer, isoprene-butadiene copolymer, isoprene-styrene copolymer, terpolymer of styrene-isoprene-butadiene, acrylonitrile-butadiene rubber, terpolymer of acrylonitrile-butadiene-styrene, or combinations thereof.

13. The composition of claim 9, wherein the compound is bis-[2-(2-oxazolyl)-phenyl] disulfide 14. The composition of claim 9, wherein the mineral filler is silica, talc, kaolin, clay, metal oxides, aluminum hydrate, mica, or mixtures thereof.

15. The composition of claim 9, wherein the cure agent includes sulfur and at least one accelerator.

16. A tire comprising at least one component that comprises the composition of claim 9.

17. The tire of claim 16, wherein the component is a tire tread.

* * * * *